US009254242B2

(12) United States Patent
Mueller et al.

(10) Patent No.: US 9,254,242 B2
(45) Date of Patent: Feb. 9, 2016

(54) CONNECTOR DEVICE

(71) Applicant: Roche Diagnostics International AG, Rotkreuz (CH)

(72) Inventors: Marcel Mueller, Therwil (CH); Maurice Ducret, Burgdorf (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 121 days.

(21) Appl. No.: 14/049,329

(22) Filed: Oct. 9, 2013

(65) Prior Publication Data
US 2014/0034185 A1   Feb. 6, 2014

Related U.S. Application Data

(63) Continuation of application No. PCT/EP2012/053579, filed on Mar. 1, 2012.

(30) Foreign Application Priority Data

Apr. 12, 2011   (EP) ..................................... 11162006

(51) Int. Cl.
*A61J 1/20* (2006.01)
*A61M 39/00* (2006.01)
*A61M 39/14* (2006.01)

(52) U.S. Cl.
CPC *A61J 1/2089* (2013.01); *A61J 1/20* (2013.01); *A61J 1/201* (2015.05); *A61J 1/2013* (2015.05); *A61J 1/2048* (2015.05); *A61J 1/2051* (2015.05); *A61J 1/2055* (2015.05); *A61J 1/2065* (2015.05); *A61M 39/14* (2013.01); *A61M 2039/0027* (2013.01)

(58) Field of Classification Search
CPC ......... A61J 1/20; A61J 1/2006; A61J 1/2048; A61J 1/2051; A61J 1/2089
USPC ........................... 141/319, 329, 383; 604/413
See application file for complete search history.

(56) References Cited

U.S. PATENT DOCUMENTS 3,872,867 A *  3/1975  Killinger ....................... 604/413
4,585,439 A    4/1986  Michel
4,759,756 A *  7/1988  Forman et al. ................ 604/413
(Continued)

FOREIGN PATENT DOCUMENTS

DE   102005006771 A   8/2006
EP       0143895 A1   6/1985
(Continued)

*Primary Examiner* — Timothy L Maust
(74) *Attorney, Agent, or Firm* — Roche Diabetes Care, Inc.

(57) ABSTRACT

A connector device for connecting two containers with first and second members slidably displaceable in regard to each other along an axis between a first and a second position is presented. The first member comprises a needle parallel to the axis so that the first container's septum is penetrated by one end of the needle when the first container is introduced into the first member. The second member comprises a coupling to the second container. The other needle end penetrates the second container's septum when the members are in the second position establishing a connection between the two containers. The first member comprises a coupling to the second container coupled to the second member. The first member can couple to the second container when the two members are in the second position and cannot couple to the second container when the two members are in the first position.

27 Claims, 12 Drawing Sheets

(56) References Cited

U.S. PATENT DOCUMENTS

| | | | |
|---|---|---|---|
| 5,445,631 A * | 8/1995 | Uchida | 604/412 |
| 5,478,337 A * | 12/1995 | Okamoto et al. | 604/413 |
| 5,989,237 A * | 11/1999 | Fowles et al. | 604/413 |
| 6,453,956 B2 * | 9/2002 | Safabash | 141/329 |
| 6,852,103 B2 | 2/2005 | Fowles et al. | |
| 6,890,328 B2 * | 5/2005 | Fowles et al. | 604/413 |
| 7,074,216 B2 * | 7/2006 | Fowles et al. | 604/413 |
| 7,077,835 B2 * | 7/2006 | Robinson et al. | 604/413 |
| 7,628,779 B2 | 12/2009 | Aneas | |
| 8,915,902 B2 * | 12/2014 | Reynolds et al. | 604/413 |
| 2010/0241088 A1 * | 9/2010 | Ranalletta et al. | 604/264 |
| 2012/0123382 A1 | 5/2012 | Kubo | |
| 2014/0034185 A1 * | 2/2014 | Mueller et al. | 141/1 |

FOREIGN PATENT DOCUMENTS

| | | |
|---|---|---|
| EP | 1219283 A2 | 7/2002 |
| EP | 2445058 A1 | 5/2012 |
| JP | 2011019704 A | 5/2012 |
| WO | 03/070147 A2 | 8/2003 |

\* cited by examiner

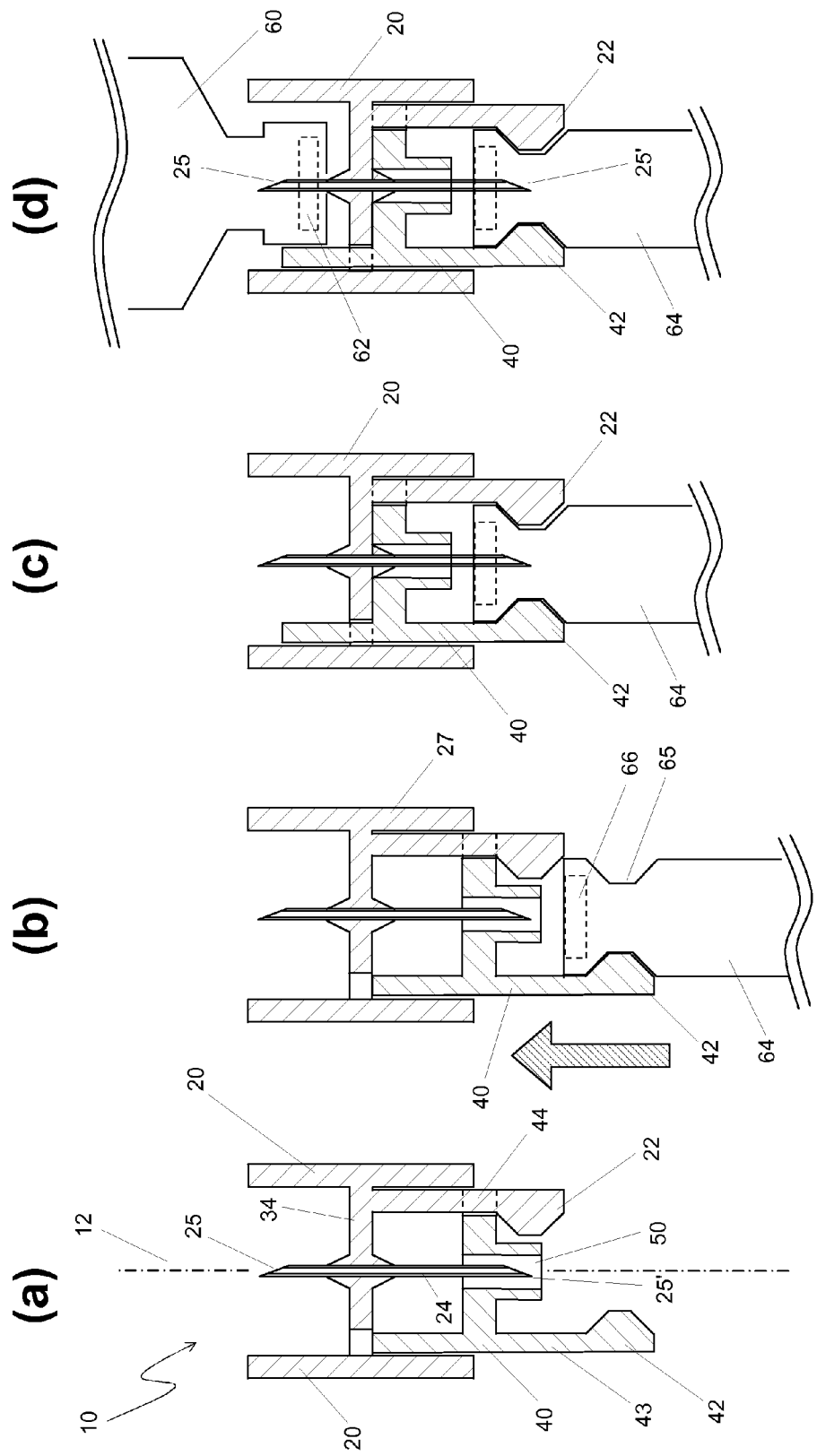

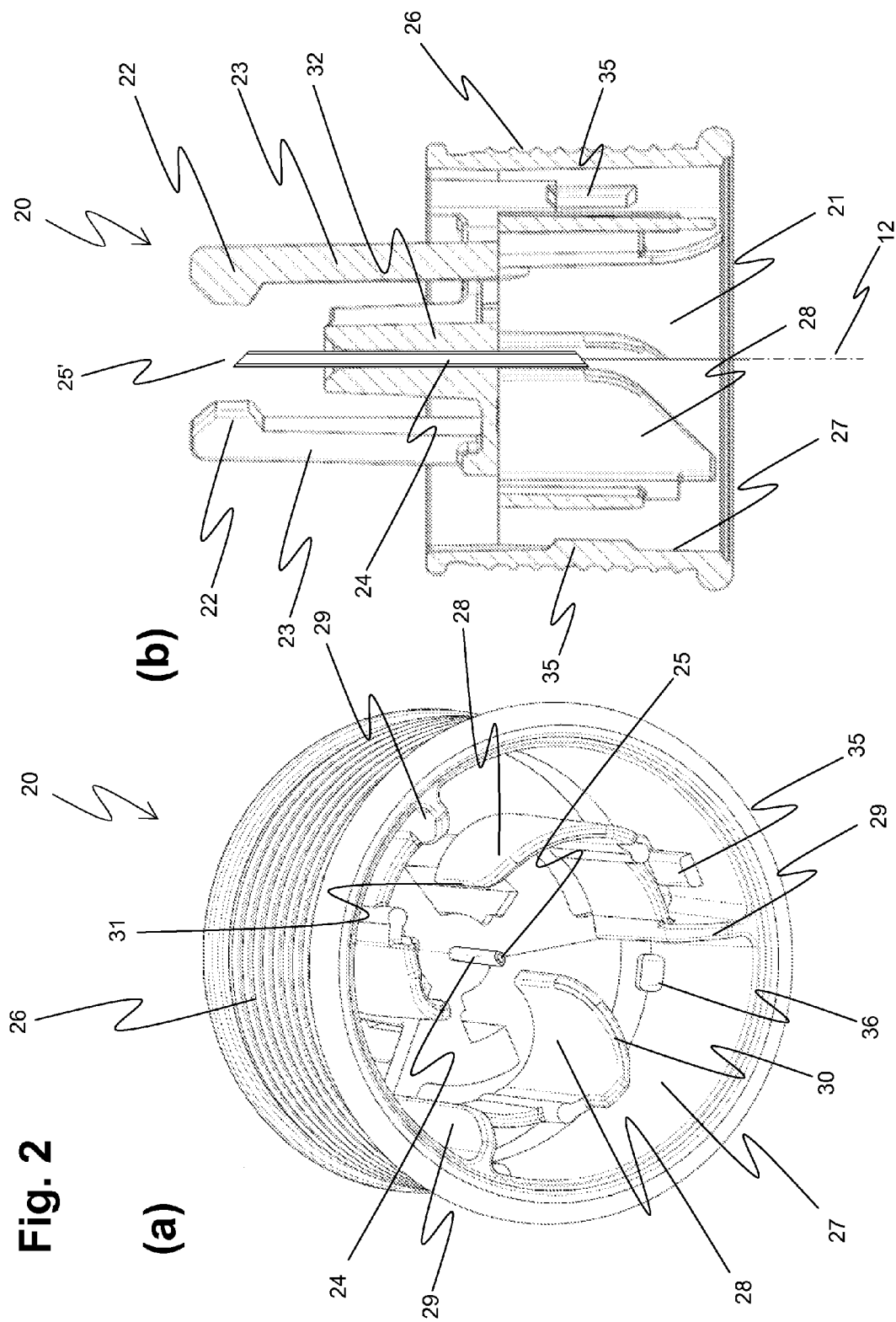

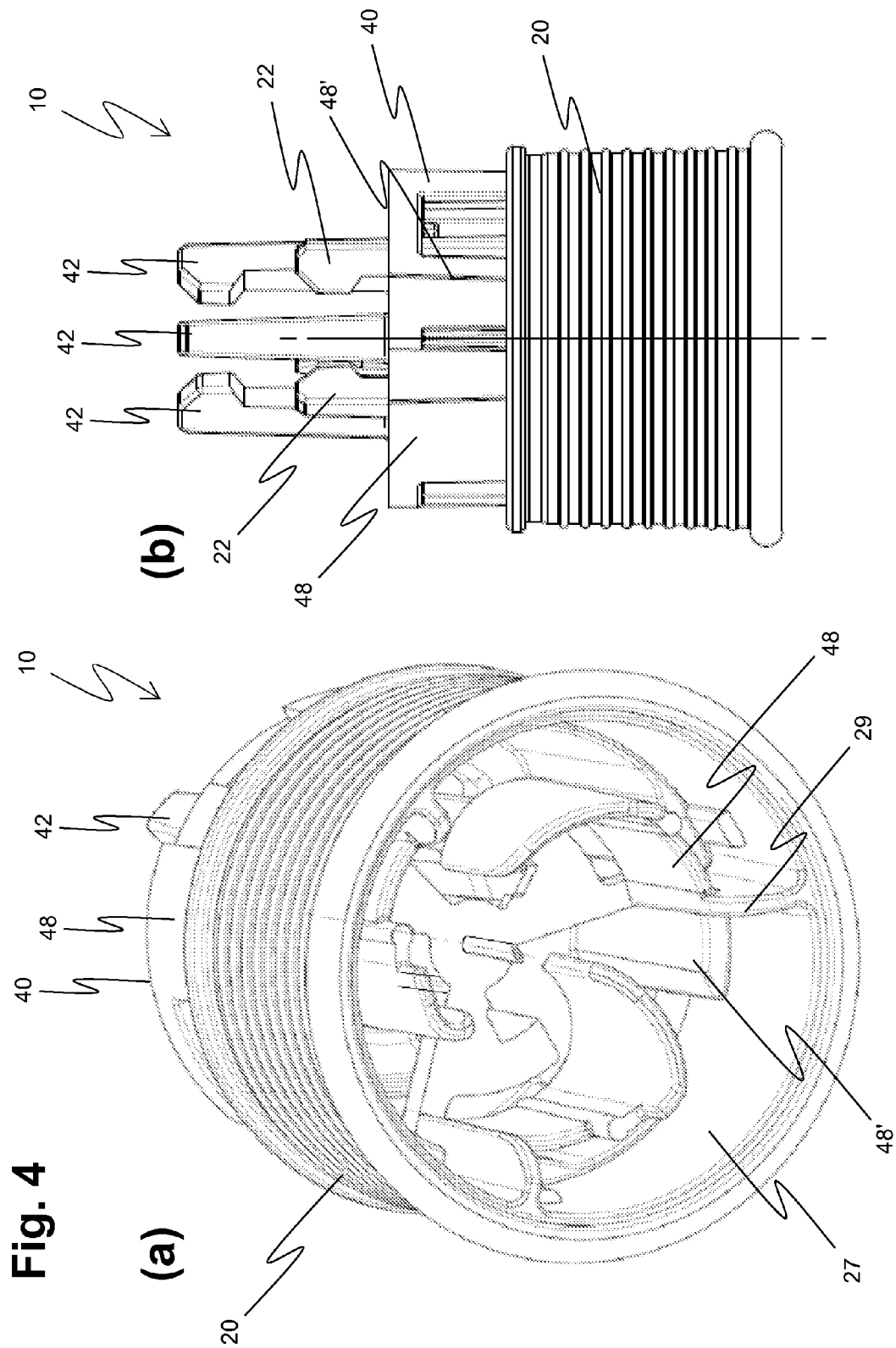

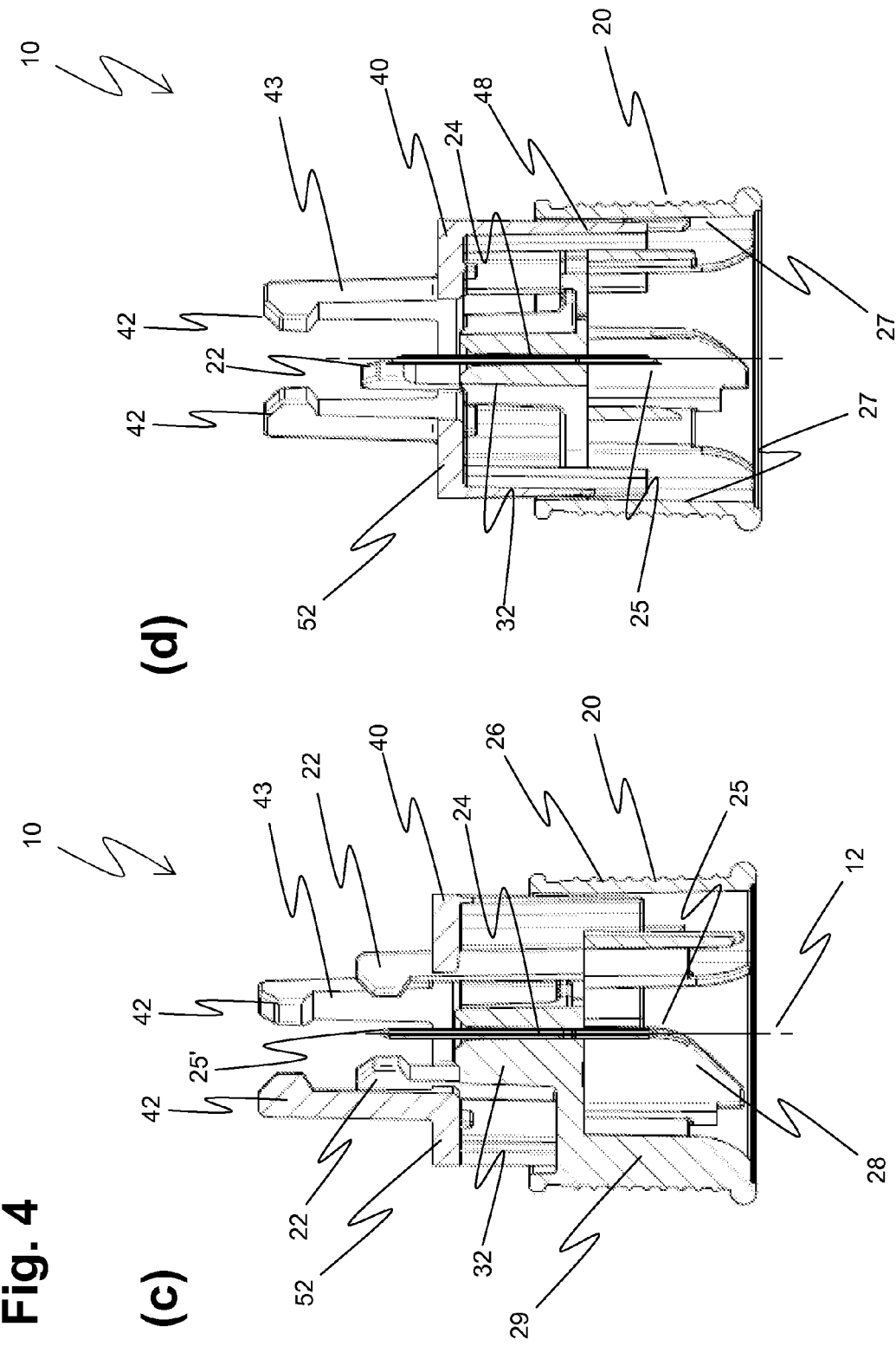

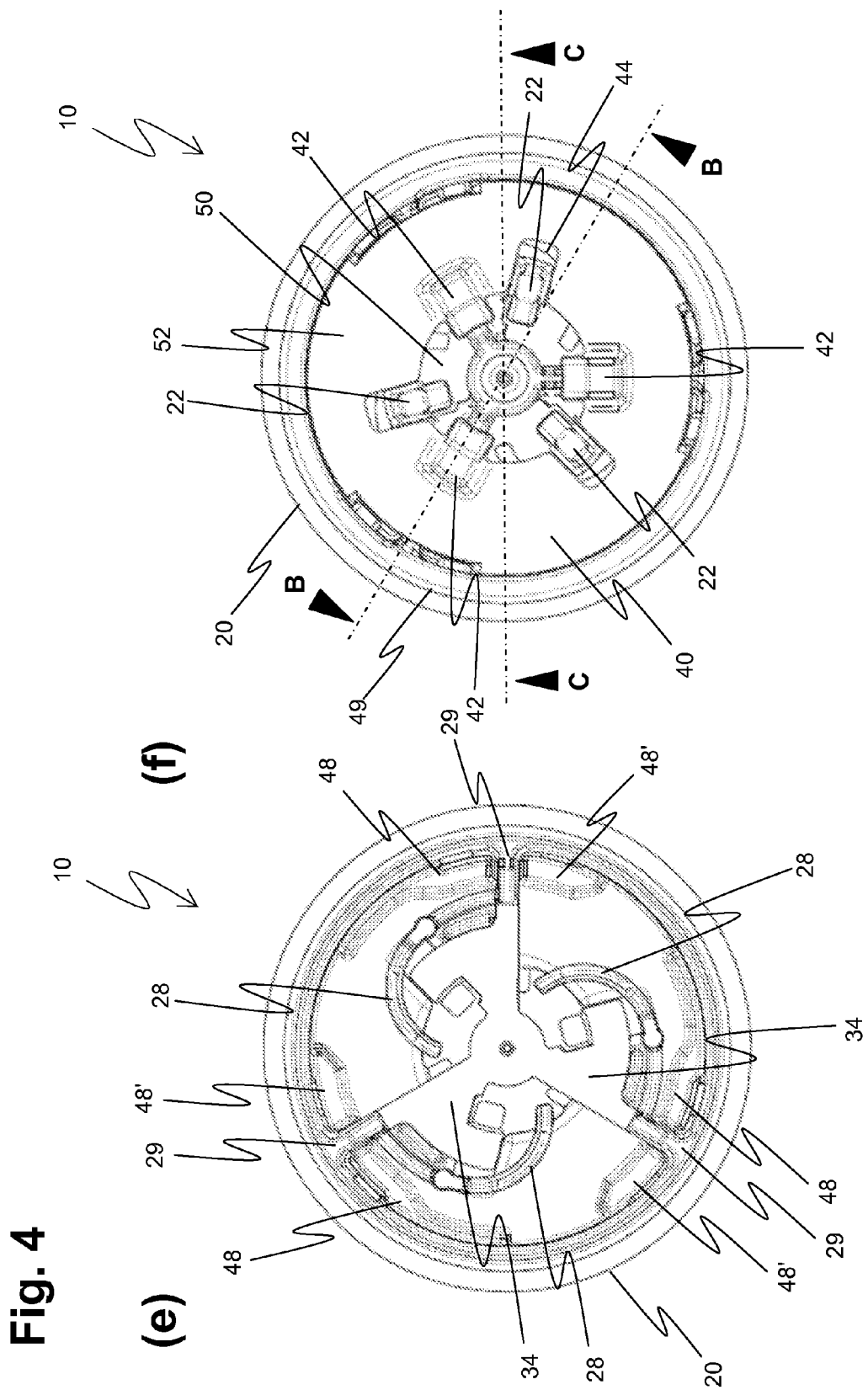

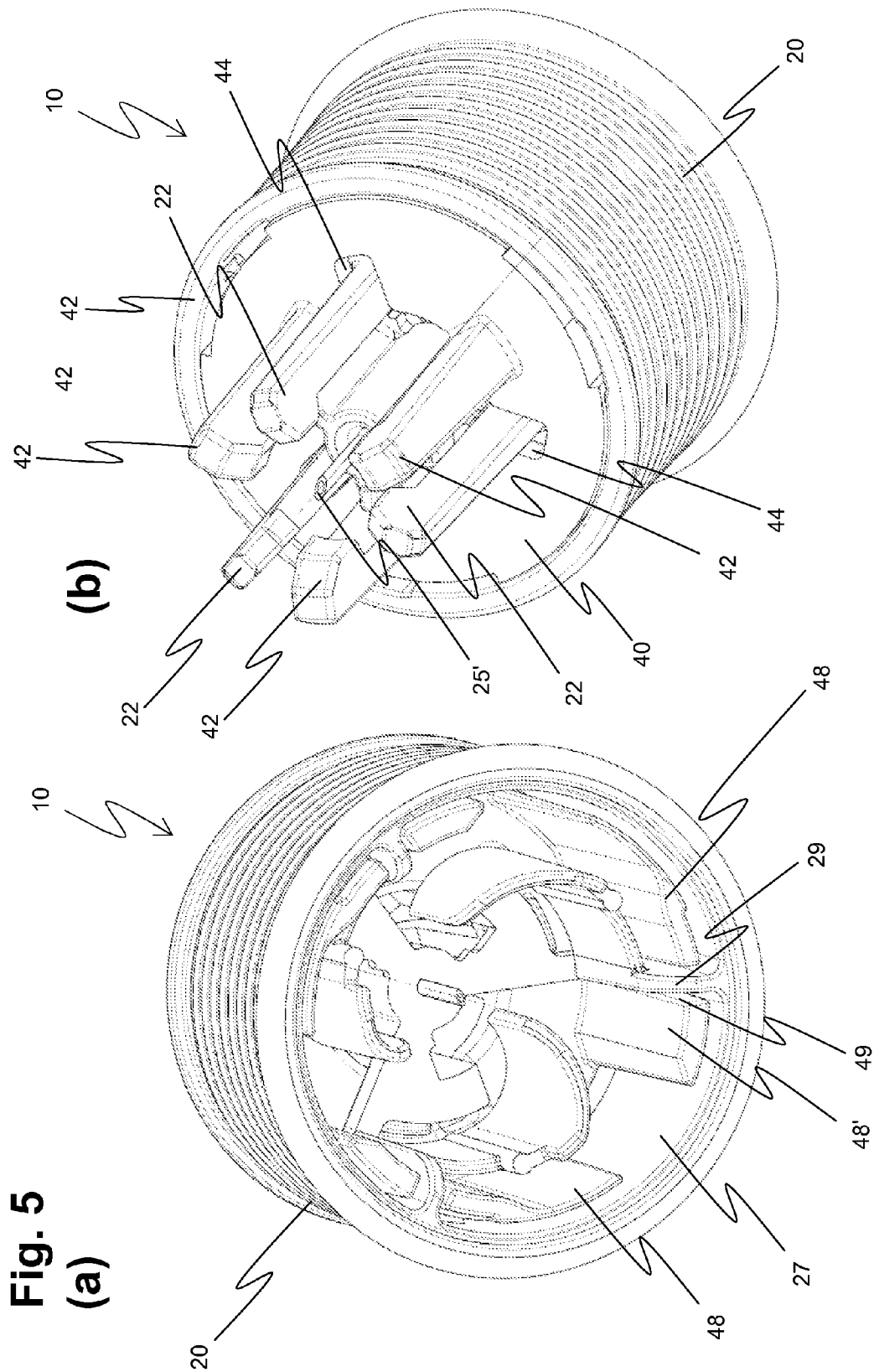

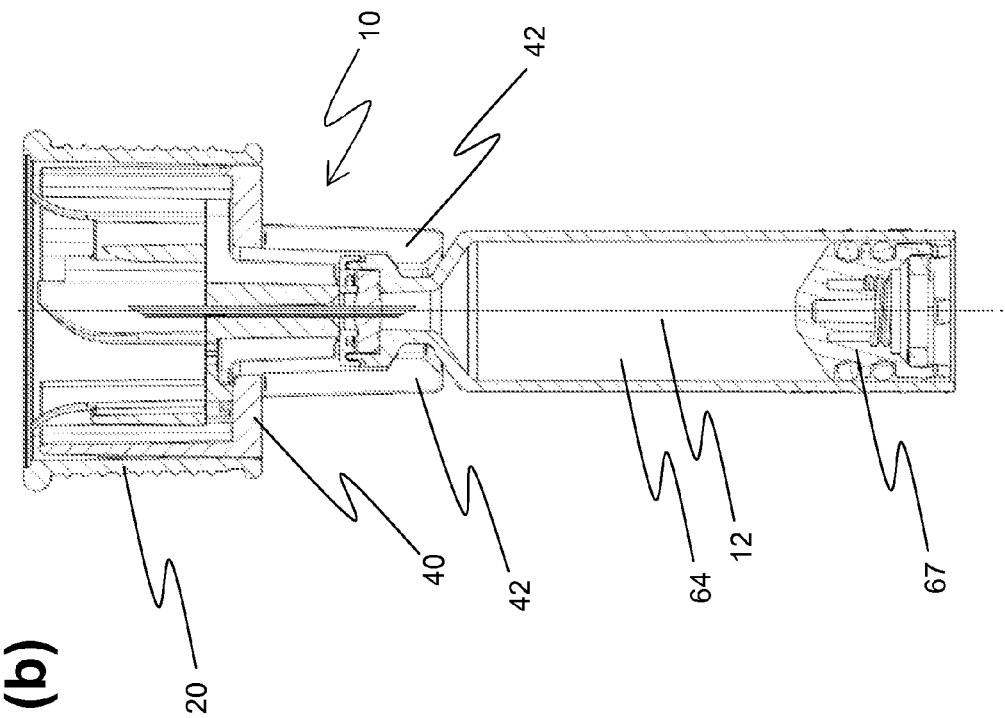
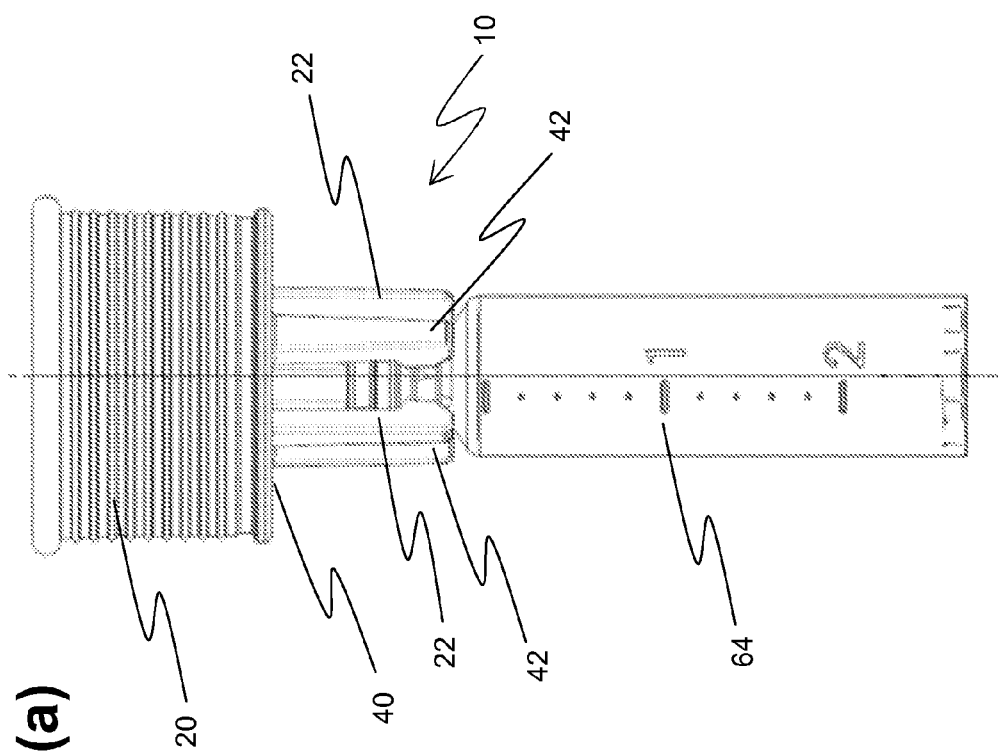
Fig. 7

CONNECTOR DEVICE

CROSS-REFERENCE TO RELATED APPLICATIONS

This application is a continuation of PCT/EP2012/053579, filed Mar. 1, 2012, which is based on and claims priority to EP 11162006.8, filed Apr. 12, 2011, which is hereby incorporated by reference.

BACKGROUND

The present disclosure generally relates to a connector device and, in particular, to a connector device for establishing fluid communication between two septum sealed containers, a septum sealed container, a kit with such a connector device, and a method for transferring liquid between two septum sealed containers.

In the medical field, there is a need to transfer liquid medicaments or other medical related liquids from one container to another. For example, medical personnel routinely draw liquid medicaments from vials into syringes in order to inject the medicament to a patient.

In cases where users without professional training have to carry out such tasks, there is even a more pronounced need for such a liquid medicament transfer process to be easy, quick, inexpensive, and most importantly safe. This is for example the case in the field of diabetes therapy by continuous subcutaneous insulin infusion, where a person with diabetes carries an insulin infusion pump device continuously night and day.

In a common type of such ambulatory infusion pump devices, a disposable reservoir container is provided that holds the liquid medicament required for some days. These disposable reservoir containers typically comprise a cylinder and a piston that is slidably arranged in the cylinder. Such containers are available prefilled by the manufacturer. Alternatively, they are provided empty and filled by the user with content from another supply container such as a vial or an injection pen cartridge.

One well-known technique to transfer liquid medicament is by the use of a syringe, where the liquid is first transferred from the septum sealed supply container to the syringe, and subsequently transferred from the syringe to the disposable reservoir container. A common type of disposable reservoir container for infusion pump devices comprises a male luer connector for connecting the cylinder to the infusion line, which can also be connected to a needle for filing purposes. Thus with a removable piston shaft and a disposable needle attached to the luer connector, such containers can be directly manually filled like a syringe without the need for an additional syringe.

The filling procedure is generally carried out by an untrained person, such as the patient or a relative. The proper use of syringes and needles requires certain manual skills Many patients with motor difficulties, such as diabetics with neuropathy or the elderly, have problems with the safe handling of syringes. In addition, accidental needle injuries, safe disposal of used needles, air free filling, and transferring the proper amount of medication without unnecessary waste are always a concern. Another problem is cross-contamination of medications between containers.

To avoid the use of a syringe with a needle for filling the disposable reservoir container, a connector device with a protected transfer needle can be used. A first member of the connector device is intended to be releasably attached to a septum sealed supply container, e.g. a vial or an injection pen cartridge, containing the liquid medicament. A second member is slideably arranged in the first member and comprises a female luer connector that can be connected to a corresponding male luer connector of a disposable reservoir container. Furthermore, it comprises a hollow transfer needle for penetrating the septum of the supply container. Prior to use, the members are in a first position, with the transfer needle of the second member being protected by the first member. After attaching the first member to the supply container, and the second member to the disposable reservoir container, the second member is pushed toward the supply container. The transfer needle penetrates the septum of the supply container, and a fluid connection between disposable reservoir container and supply container is established.

For several reasons, such as for example reusability and maintenance of sterility, the use of disposable reservoir containers that are provided sealingly closed by a septum is preferable over containers with luer connectors.

A variant of the above-mentioned connector device that allows the transfer of liquid between two septum sealed containers is known, intended to allow dissolving a solid medicament provided in a vial with liquid from an infusion bag and transferring the liquid with the reconstituted medicament back into the infusion bag.

A first cylindrically shaped member is slidably mounted in a second cylindrically shaped member and comprises a receptacle for releasably connecting to the neck of a septum sealed infusion bag. A transfer needle with two pointed ends is mounted on the first member. One half of the needle is located in the receptacle of the first member while the second half of the transfer needle is located inside of the second member. The second member comprises locking means for permanently attaching a septum sealed vial, and a seal that encloses the second end of the needle and also sealingly encloses the septum of the vial when connected to the second member.

When the first container is releasably inserted into the first member, the first end of the needle penetrates the septum of the container. A fluid connection between infusion bag and transfer needle is established. After the second container has been permanently attached to the second member, the two members are rotated around their axis, thereby going from a deactivated state, where the members cannot be shifted, to an activated state of the connector device, where the members can be shifted in regard to each other. The first member can now be pushed into the second member, and the second end of the needle penetrates first the seal of the second member and then the septum of the second container. A fluid connection between the two containers is established, and liquid can be transferred from the first container to the second container, and back.

Therefore, there is a need for a connector device for fluidly connecting two septum sealed containers that are releasably connectable to at least one septum-sealed container without having its seal penetrated, where the connector device is easily removable, allows simple and safe handling also for untrained users, is reliable and producible at low cost, and has a long shelf-time.

SUMMARY

According to the present disclosure, a connector device and method for fluidly connecting two containers with two members that are slidably displaceable in regard to each other along an axis between a first and a second position is presented. The connector device can comprise a first member comprising a needle with two ends arranged parallel to the axis in such a way that a septum of the first container is penetrated by one end of the needle when the first container is introduced into a receptacle of the first member and a second member comprising a releasably coupling to a second container wherein the other end of the needle does not come into contact with a septum of the second container coupled to the second member when the members are in the first position and the other needle end penetrates the septum of the second container when the members are in the second position establishing a fluid connection between the two containers. The first member comprises a releasably coupling to the second container that is coupled to the second member. The coupling of the first member can couple to the second container when the two members are in the second position and cannot couple to the second container when the two members are in the first position.

Accordingly, it is a feature of the embodiments of the present disclosure to provide a connector device for fluidly connecting two septum sealed containers that are releasably connectable to at least one septum-sealed container without having its seal penetrated, where the connector device is easily removable, allows simple and safe handling also for untrained users, is reliable and producible at low cost, and has a long shelf-time. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIGS. 1a-d illustrate schematically a connector device in a cross-sectional view, (a) in a first, initial position prior to use, (b) in the first position with the second member being connected to a septum-sealed disposable reservoir container, (c) in a second position, where both the first member and the second member are connected to the disposable reservoir container, and (d) with the connector device being connected to a second septum-sealed supply container according to an embodiment of the present disclosure.

FIGS. 4a-f illustrate the assembled connector device of FIGS. 2 and 3 in the first position, (a) in a perspective view from below, (b) in a side view, (c) in a cross-sectional view along B-B, (d) in a cross-sectional view along C-C, (e) in a bottom view, and (f) in a top view according to an embodiment of the present disclosure.

FIGS. 7a-b illustrate the connector device of FIGS. 2 and 3 in a second position, where also the first member is coupled to the disposable reservoir cartridge, and the hollow transfer needle penetrates the septum of the cartridge, (a) in a side view, and (b) in a cross-sectional view according to an embodiment of the present disclosure.

DETAILED DESCRIPTION

Figure 2:
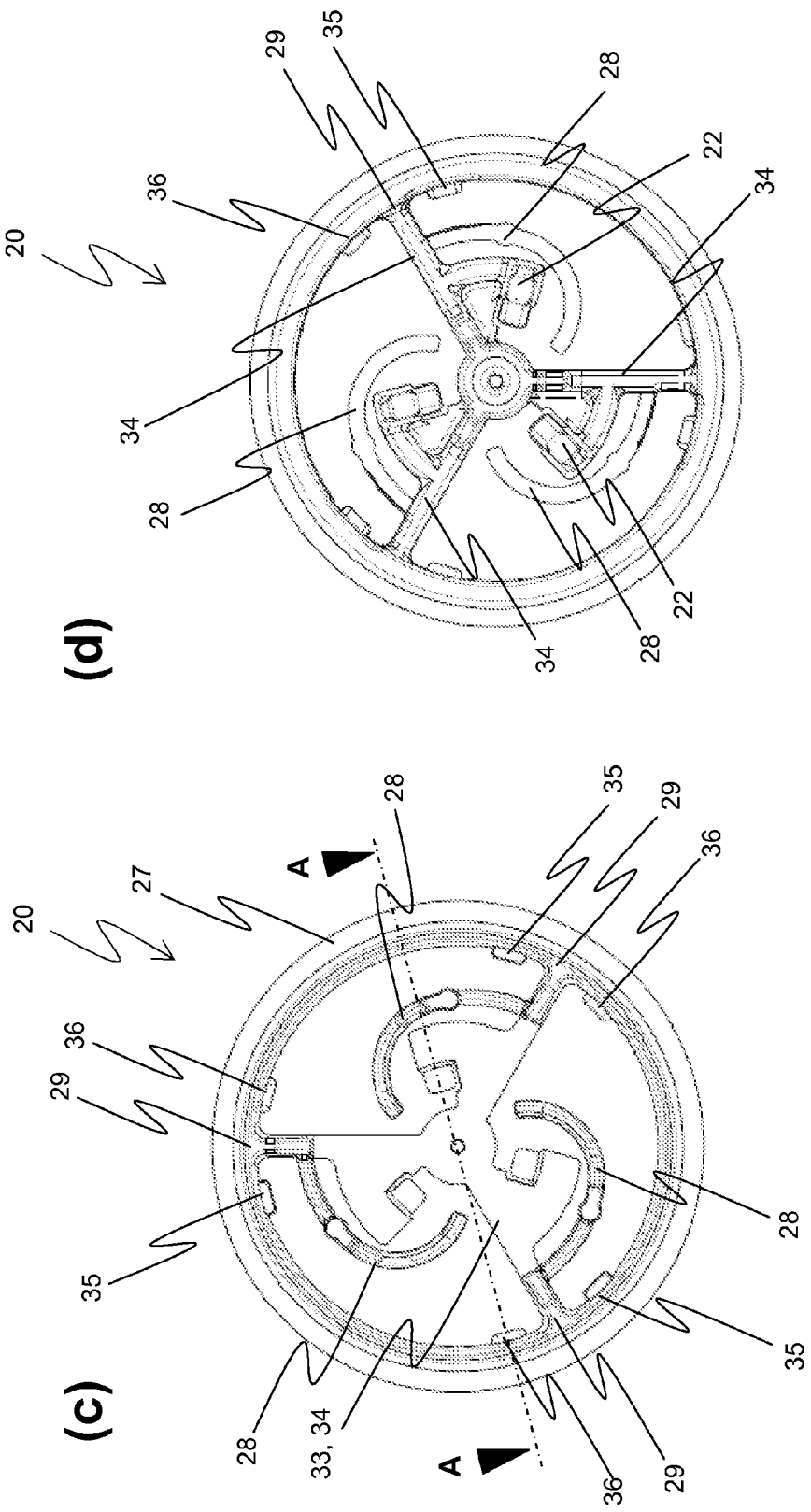
FIGS. 2a-d illustrates the first member an connector device, (a) in a perspective view from below, (b) in a cross-sectional view along A-A, (c) in a bottom view, and (d) in a top view according to an embodiment of the present disclosure.
Figure 3:
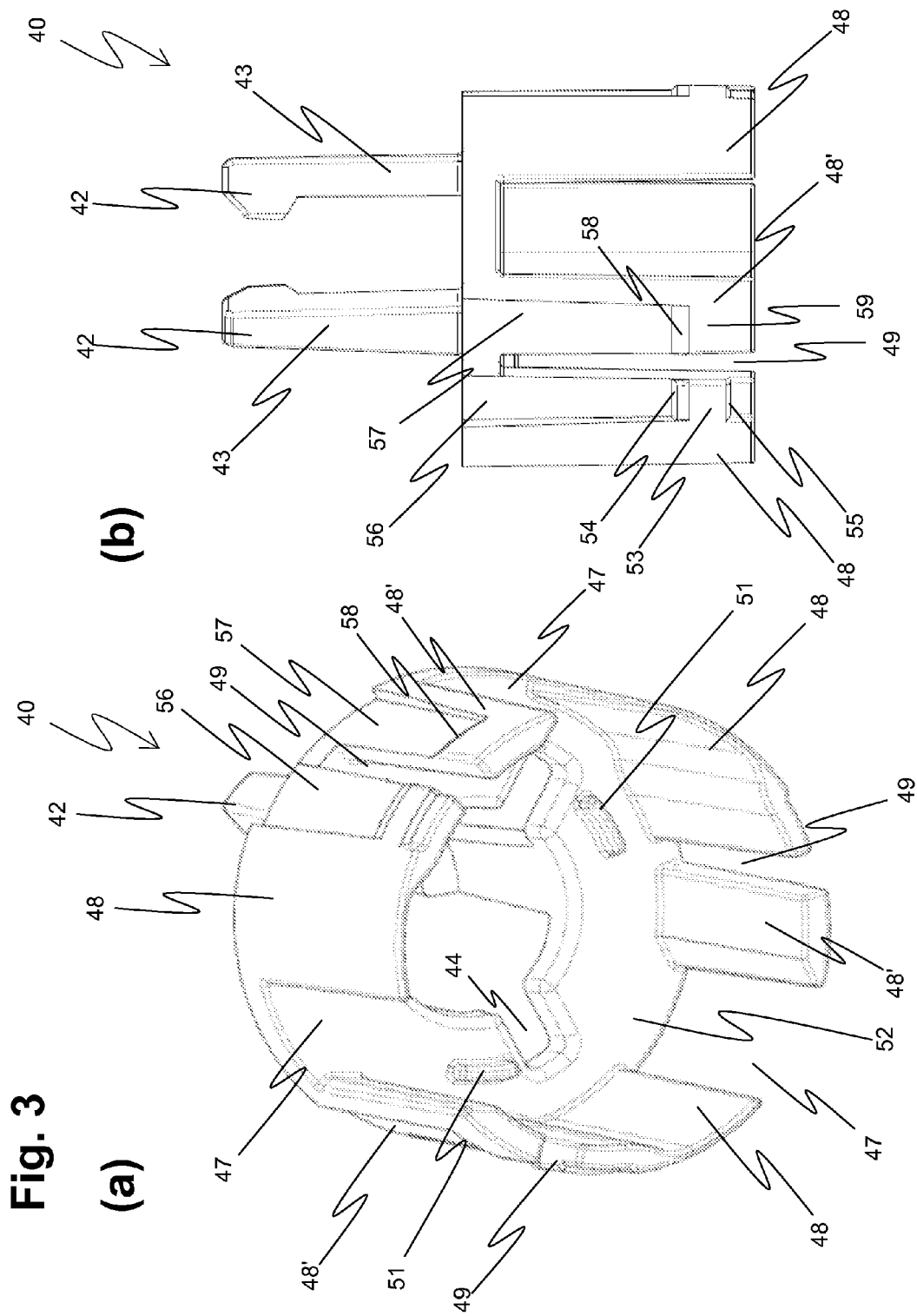
FIGS. 3a-d illustrate the second member of the same connector device, (a) in a perspective view from below, (b) in a side view, (c) in a bottom view, and (d) in a top view according to an embodiment of the present disclosure.
Figure 3:
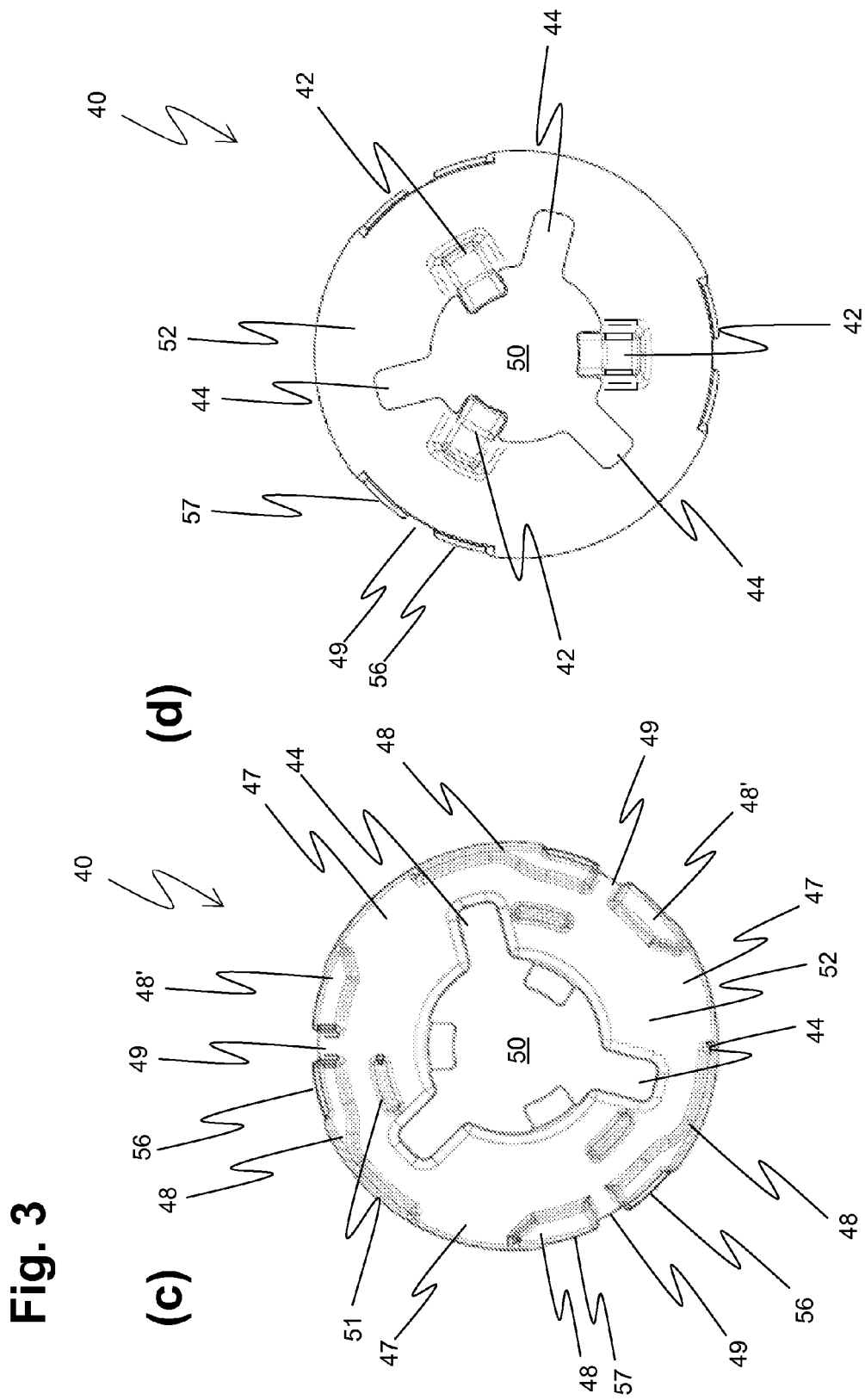

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A connector device for fluidly connecting two septum sealed containers can comprise two members that can be slidably displaceable in regard to each other along an axis between a first and a second position. A first member can comprise a hollow transfer needle with two pointed ends arranged parallel to the axis in such a way that a septum of a first one of the two containers can be penetrated by one end of the needle when the first container is introduced into a receptacle of the first member. A second member can comprise a releasably coupling to the second one of the two containers. The other end of the needle may not come into contact with a septum of the second container coupled to the second member when the members are in the first position. The other needle end can penetrate the septum of the second container when the members are in the second position establishing a fluid connection between the two containers. The first member can comprises a releasably coupling to the second container that can be coupled to the second member. The coupling of the first member can couple to the second container when the two members are in the second position and cannot couple to the second container when the two members are in the first position.

One advantage of such a connector device can be the fact that in the second position, where a fluid communication between the two containers is established and the user may have to carry out manual operations steps, there can be a stable lock between the connector device and the disposable cartridge. There is further no need for locking the two members in regard to each other in the second position, since the two members can be locked indirectly via the cartridge. This can allow a simpler construction of the connector device and also can ease assembling and disassembling of the connector device.

Advantageously, such a connector device can be made from a material that can provide certain flexibility. Suitable materials can be, for example, thermoplastic polymers. The connector devices can be manufactured by injection molding.

In one embodiment of a connector device, the coupling of the second member can comprise a multitude of pawls that can engage with a neck of the second container.

In another embodiment of a connector device, the coupling of the first member can comprise at least one pawl that can be able to engage with a neck of the second container.

Advantageously, the coupling of the first member can comprise a multitude of pawls that can engage with a neck of the second container.

In a further embodiment of a connector device, both the coupling of the first member and the coupling of the second member can comprise a multitude of pawls that can engage with a neck of the second container.

In one embodiment, the pawls of the first member can run in slots provided on the second member.

In yet another embodiment of a connector device, the first member can comprise a guiding structure and the second member can comprise a guiding structure. The two guiding structures can abut on each other.

One of the guiding structures of the two members can comprise a handle or grip area for safely holding the device during operation.

The guiding structure of one of the two members of a connector device can comprise one or more guiding ribs that can run in guiding slots of the guiding structure of the other one of the two members.

In yet a further embodiment of a connector device, the guiding structure of one of the two members can be provided with one or more cams that can run in grooves on the guiding structure of the other one of the two members.

Advantageously, in one embodiment, a stopper can be provided in the one or more grooves, which can restrict the movement of the cam in the groove in one or two directions.

An embodiment of a connector device can comprise a septum sealed container coupled to the second member of the connector device. The two members can be in the first position.

A septum sealed container can comprise a connector device. Such a container can be used for storing a liquid a solid or a semi-liquid substance depending on the application.

In an embodiment of such a container, the two members of the connector device can be in the first position and the second member of the connector device can be coupled to the container.

A kit can comprise one or more connector devices and one or more septum sealed containers. The couplings of the two members can be coupled to the septum sealed containers.

In a method for transferring liquid between two septum sealed containers, a connector device can be provided. The two members of the connector device can be in the first position. The first member of the connector device can be attached to a first container, thereby penetrating the septum seal of the first container with the hollow transfer needle of the first member and establishing a fluid connection between first container and hollow transfer needle. A second container can be coupled to the second member of the connector device. The two members can be shifted in regard to each other from the first position to the second position, thereby penetrating the septum seal of the second container with the hollow transfer needle of the first member and establishing a fluid connection between second container and hollow transfer needle.

In an embodiment of the method, the containers can be attached in reversed order. Thus a connector device can be provided, the two members of the connector device being in the first position. A second container can be coupled to the second member of the connector device. The first member of the connector device can be attached to a first container, thereby penetrating the septum seal of the first container with the hollow transfer needle of the first member and establishing a fluid connection between first container and hollow transfer needle. The two members can be shifted in regard to each other from the first position to the second position, thereby penetrating the septum seal of the second container with the hollow transfer needle of the first member and establishing a fluid connection between second container and hollow transfer needle.

In another embodiment of the method, a connector device can be provided, the two members of the connector device being in the first position. A second container can be coupled to the second member of the connector device. The first member of the connector device can be attached to a first container and at the same time the second container can be pushed toward the first member. As a result, the two members can be shifted in regard to each other from the first position to the second position, thereby penetrating the septum seal of the second container with the hollow transfer needle of the first member and establishing a fluid connection between second container and hollow transfer needle, while at the same time the hollow transfer needle of the first member can penetrate the septum seal of the first container and can establish a fluid connection between first container and hollow transfer needle.

Referring initially to FIG. 1, the basic function of a connector device 10 can be understood, where an exemplary embodiment of such a connector device 10 is shown during different phases of normal operation.

The connector device 10 in an initial first position, prior to use, is depicted in FIG. 1(a). A first member 20 and a second member 40 can be arranged in regard to each other in such a way that they can be displaceable along a common axis 12. The two members can be engaged to limit both off-axis movement and rotational movement. For that purpose, interacting guides can be provided on the two members.

A hollow transfer needle 24 with two tips 25, 25' can be mounted in the center of a supporting structure 34 of the first member 20 of the device. The guiding structure 27 of the first member 20 can provide protection against damage of a first end 25 of the needle and accidental needle injuries. The other, second end 25' of the needle 24 can be arranged in a central opening 50 of the second member 40 of the device. Three pawls 42, of which one is visible in the cross section, can be circumferentially arranged around the central opening of the second member 40. These pawls can engage with the neck of a disposable reservoir container, thereby providing a releasable connection to the container. Similarly three pawls 22 (of which one is visible in the cross section) can be circumferentially arranged on the first member 20 and can protrude through openings 44 in the supporting structure of the second member.

In a first step, a disposable reservoir container, namely an empty cartridge 64 sealingly closed by a septum 66, can be coupled to the connector device 10, as shown in FIG. 1(b). For that purpose, the neck 65 of the container can be pushed into the center of the resilient pawls of the second member 40. The multitude of pawls 42 of the second member 40 can snap into the groove of the neck 65, thereby releasably locking the container 64 to the second member. The connector device 10 can still be in its first position, in which the septum 66 can remain unpunctured by the hollow transfer needle 24 and the pawls of the first member cannot lock to the cartridge 64.

The disposable empty cartridge 64, intended to be filled with a liquid such as a liquid medicament from a supply container 60, can either be coupled to the connector device 10 by the user himself, prior to the filling procedure, or can be provided preassembled by the manufacturer with an already mounted connector device. The latter variant can be advantageous for various reasons, for example improved handling, since the omission of a manual assembling step can reduce the risk of operating errors and injuries. Furthermore, the disposable reservoir container 64 and the connector 10 can be provided already preassembled, for example in a sterilized blister packaging. Since the septum is not penetrated during the storage after manufacture, its ability to sealingly close around the transfer needle during operation cannot be compromised by long-term deformation of the elastomeric septum. As a result, the shelf-time of the disposable container may not be negatively affected.

When a disposable reservoir container 64 is to be filled with liquid medicament, the container 64 can be fluidly connected to the transfer needle. The container, together with the coupled second member 40, can be manually pushed toward the first member 20 of the connector device along axis 12. The second member 40 can be positively locked to the container 64. The device can be in the first position.

Pushing the cartridge 64 further along axis 12, the second member 40 can slide into the first member 20 and the resilient pawls 22 of the first member 20 can snap into the groove of the neck 65, thereby positively locking the container 64 to the first member 20. At the same time, the second tip 25' of the hollow needle 24 can penetrate the septum 66 of the container 64 establishing a fluid connection between the hollow needle and the inside of the container. The connector device 10 can now be temporarily locked in the second position, as shown in FIG. 1(c). The linear motion of the two members and the cartridge during the connection step can prevent the needle from exerting a shear force on the seal, potentially damaging the septum seal.

In a subsequent third step, the connector device can now be coupled to the supply container 60, sealingly closed by a septum 62, by attaching the first member 20 to the top end of the container. For that purpose, the connector device, particularly the first member, can be provided with guides and/or couplings. The first tip 25 of the needle can penetrate the septum 62 and a fluid connection between container 60 and needle 24 can be established, as seen in FIG. 1(d). The two containers 60, 64 can now be fluidly connected via the transfer needle 24 and liquid can be transferred between the containers. In the case of an initial empty cartridge 64, liquid, e.g. liquid medicament such as insulin, can be transferred from a supply container such as a vial or an injection pen cartridge 60 to the disposable cartridge 64.

After the disposable cartridge 64 has been filled, the supply container 60 can be removed from the connector device 10. Then the disposable cartridge 64 can be removed from the connector device 10, by pulling it off. The disposable cartridge 64 can now be used in an infusion pump device and the connector device 10 can be disposed.

Although normally the disposable cartridge 64 can be fully filled before the supply container 60 is empty, it may occur that the supply container can be emptied first, particularly if small injection pen cartridges are used as a supply container. In such a case, the supply container may be disconnected and replaced while the partially filled disposable cartridge can remain connected. After a new container 60 has been connected to the device, the filling process of the disposable cartridge can be continued.

Instead of connecting the disposable cartridge to the connector device first, it can also be possible to connect in a first step the supply container to the first member and in a second step the disposable cartridge to the second member.

In yet another embodiment, the two containers can be connected to the corresponding members of the connector device while the two members can still be disassembled. Thus in a next step, the two members can be first assembled to the first position, before the members are changed to the second position and a fluid communication can be established.

The connector device can be constructed such that the connector device first changes back into its first position before it releases the disposable cartridge attached to the second member. When a user pulls apart the connector device and the cartridge 64, first the pawls 22 of the first member 20 can release the neck of the cartridge. The two members then can slide along axis 12 from the second to the first position before finally the pawls 42 of the second member 40 can release the neck 65 of the cartridge. Such an embodiment can have the advantage that during the disconnection process there may be no shear force on the septum 66 of the disposable cartridge 64, since the needle 24 can be pulled out of the septum perpendicular to the septum surface.

After removal of the disposable cartridge 64, the connector device can be back in its first position. The second needle tip 25' can again be safely located inside the second member and the connector device can be safely disposed.

If, alternatively, the connector device is constructed such that the pawls of both members can release the cartridge at the same time, the device can remain in the second position after the disconnection of the cartridge 64. However, also in this second position, the second needle tip 25' may not be accessible, since the pawls 42 cover the needle, and the device can also be safely disposed.

Another embodiment of a connector device 10 is depicted in FIGS. 2 to 5. The connector device 10 can have two members 20, 40. The first member 20 can comprise a cylindrical wall structure 27 acting as a guide for the second member 40 and as a handle for the user. The outer surface of the cylinder can have a grooved area 26 for a better grip. On one longitudinal end of the cylinder structure, a radial supporting structure 33 with a central portion 32 and three bridges 33 can be arranged. A hollow transfer needle 24 with two pointed ends 25, 25' can be mounted in the central portion aligned with a longitudinal axis 12 of the member 20. On each of the three bridges 33, a pawl 22 with a flexible, resilient arm 23 can be mounted.

On the inner wall of the cylindrical guiding structure 27, three guiding ribs 29 can be arranged parallel to the axis 12 intended to interact with corresponding slots 49 of the second member 40. Three resilient structures 28 can be mounted on the guiding ribs 29 having a bent end with a holding edge 31 and a ramp 30. When the neck 63 of a first container is introduced into the receptacle 21 of the first member, the ramps 30 can interact with the edge of the bottle neck 63 and the structures 28 can be bent outwards until finally the holding edges 31 grip the neck 63 on its circumference. Thus the three structures 28 can center the container 60 in regard to the transfer needle and also can act as a releasably coupling for the first container 60 to the connector device 10 by clamping the neck of the container. The connector can be used with differently sized supply containers, for example standard liquid medicament vials, or injection pen cartridges, since the spring-biased holding edges can adapt to different diameters of the container neck 63.

The second member 40 can comprise guiding structures 48, 48' in the form of segments of a cylinder wall to be slidably arranged in the cylinder structure 27 of the first member. Between the segments 48, 48', small guiding slots 49 can be arranged, in which the guiding ribs 29 of the first member run. Due to these guides 29, 49, the two members can be rotationally engaged, which can prevent tilting and jamming during operation, and coring of the penetrated septums. Broader gaps 47 between the segments 48, 48' can give room for the resilient structures to bend when a vial with its large neck is introduced.

The guiding structures 48, 48' can be mounted on a supporting structure 52 of the second member 40, having a central opening 50 and three adjoining slots 44. Three pawls 42 parallel to the axis 12 can be mounted on the side of the supporting structure 52 opposite to the first member. The three pawls 22 of the first member can be arranged in the three pawl slots 44, which thus also can act as guides for rotationally engaging the two members. The central portion 32 of the first member can be arranged in the central opening 50.

On the inner side of the cylindrical structure 27, three cams 35 can be provided so that in the assembled state can be located in corresponding grooves 56 on the outer side of the guiding structures 48. In one direction along axis 12, a stopper 53 can restrict the movement of the cam in the groove 56 and thus of the displacement of the first member 20 in regard to the second member 40.

Another three cams 36 can be provided on the inner side of cylindrical structure 27, which in the assembled state can be located in grooves 57 of the guiding structures 48'. Again, a stopper 59 can restrict the movement of the cam in the groove 57 and thus of the displacement of the first member 20 in regard to the second member 40.

The positions of the cams 35, 36 and the stoppers 53, 59 can be chosen in such a way that in the first position of the device the cams 35 can abut the ramp 55 of the stopper 53 and the cams 36 can abut the ramp 58 of the stopper 59. Thus the two members can be loosely fixed in the first position but may be repeatedly disassembled and reassembled without effort.

To change from the first position to the second position the resilient force on the stopper 53 has to be overcome, by sliding the cam 35 over the ramp 55. Similarly the cam 36, when engaging with the ramp 58 of the stopper 59, provides a resilient force that prevents the assembled device according to the invention to be disassembled inadvertently.

In the second position, the displacement of the members along axis 12 can be stopped when the supporting structures 33, 52 of the two members collide, which can define the second position. For a fine tuning of the second position, distance elements 51 can be provided.

For assembling the two members 20, 40 to the connector device 10, the members can be properly aligned and the guiding structures 48, 48' of the second member 40 can be introduced into the corresponding gaps between the central portion 32, the cylinder wall 27, and the bridges 33 of the first member 20. Ramp 55 of the stopper 56 can allow the cam 35 to jump over the stopper 53 during introduction of the second member.

Figure 5:
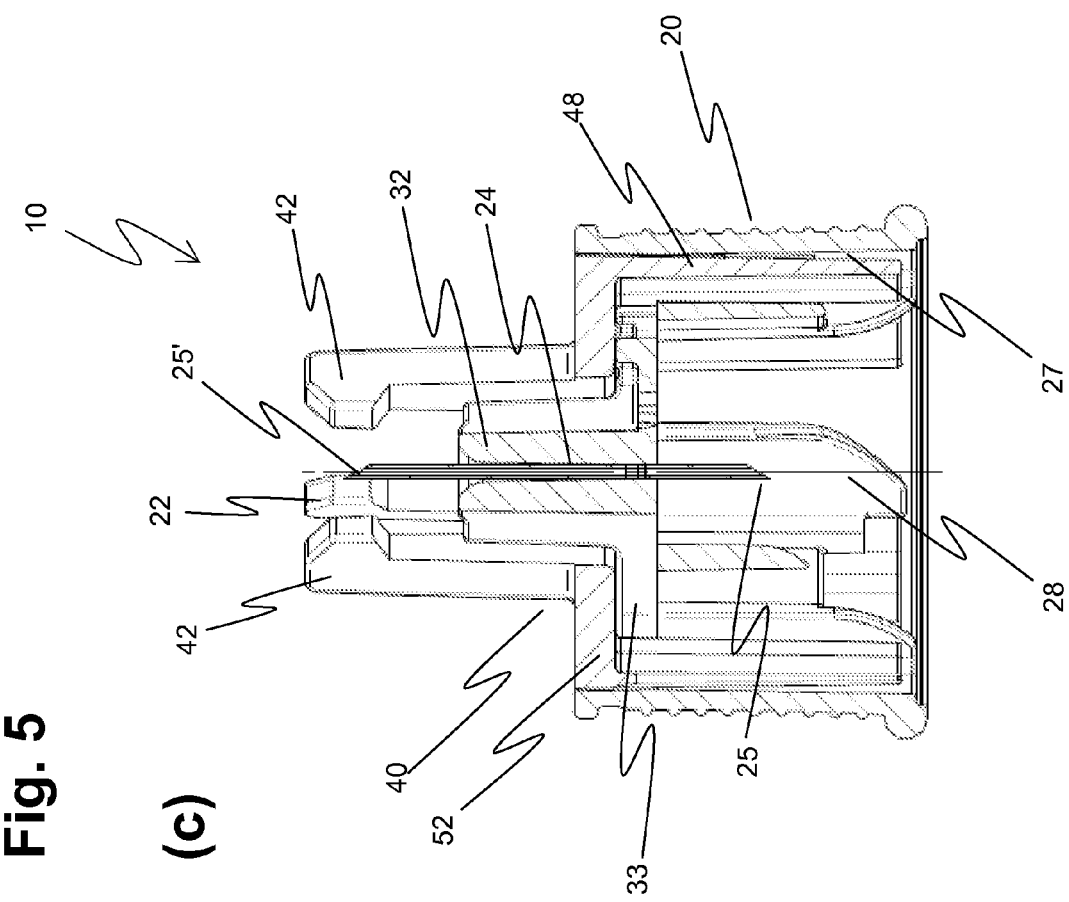
FIGS. 5a-c illustrate the assembled connector device of FIGS. 2 and 3 in the second position, (a) in a perspective view from below, (b) in a perspective view from the top, and (c) in a cross-sectional view similar to FIG. 4(c) according to an embodiment of the present disclosure. The bottom view and the top view are the same as in FIGS. 4(e) and (f).

In a first position of the connector device 10, as shown in FIG. 4, the three pawls 22 of the first member can be retracted into the device, in regard to the second member with its three pawls 42. When the second member 40 is pushed into the first member 20 eventually arriving at the second position as shown in FIG. 5, the pawls 22 can protrude toward the other pawls 42 until the heads of the two sets of pawls 22, 42 are on the same height. At the same time, the central portion 32 with the needle can protrude out of the central opening 50.

Figure 6:
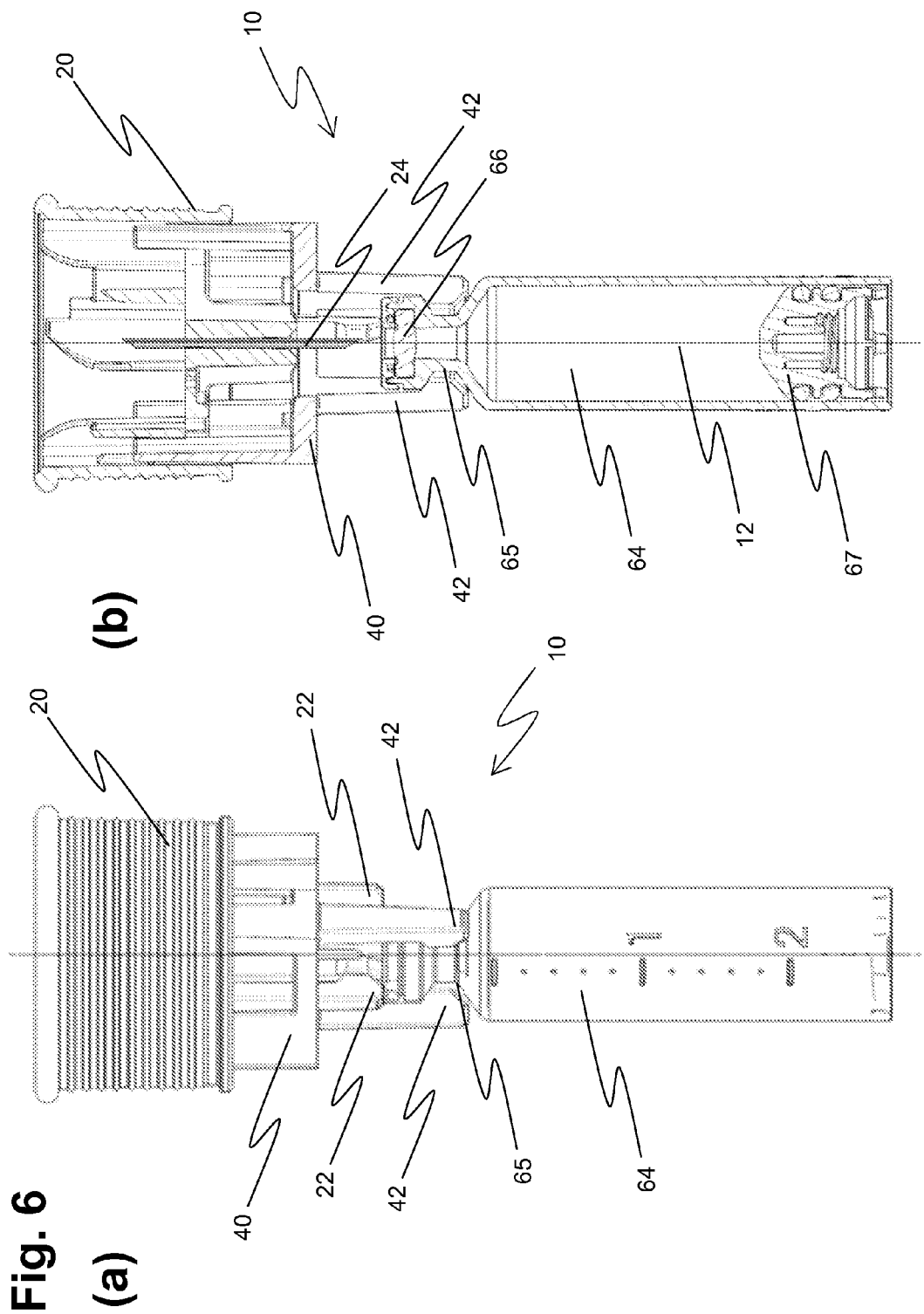
FIGS. 6a-b illustrate the connector device of FIGS. 2 and 3 in a first position prior to filling, the second member being coupled to a septum-sealed disposable reservoir cartridge, (a) in a side view, and (b) in a cross-sectional view according to an embodiment of the present disclosure.

FIG. 6 shows the connector device in a first position already coupled to an empty reservoir cartridge 64, but the septum 66 of the cartridge not yet being punctured. The three pawls 42 of the second member 40 can engage behind the neck 65 of the cartridge positively locking the cartridge to the second member. The dimensions of the pawls can be adapted to a certain type of cartridge where the pawls can tightly lock the container in both directions of the axis 12.

To connect the cartridge 64 with the needle 24, the user can push the cartridge toward the first member. The second member can glide into the first member until the pawls 22 of the first member can snap in and engage behind the neck of the cartridge thus stopping the movement. During this process, the needle 24 can have penetrated the septum 66 perpendicular to the septum surface. Container and connector device can now be fluidly connected and the connector device can be in its second position, as is shown in FIG. 7. The device is now ready for being connected to the supply container.

Instead of three and three pawls as used in the abovementioned embodiment, also other embodiments can be possible, for example two and two pawls, or two opposite pawls on the first member, and four pawls on the second member, and the like.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A connector device configured for fluidly connecting two containers with two members that are slidably displaceable in regard to each other along an axis between a first and a second position, the connector device comprising:

a first member comprising a needle with two ends arranged parallel to the axis in such a way that a septum of a first container can be penetrated by one end of the needle when the first container is introduced into a receptacle of the first member;

a second member comprising a releasable coupling to a second container wherein the other end of the needle does not come into contact with a septum of the second container coupled to the second member when the members are in the first position, and the other needle end penetrates the septum of the second container when the members are in the second position for establishing a fluid connection between the two containers;

wherein the first member comprises a releasable coupling to the second container that is coupled to the second member and wherein the coupling of the first member couples to the second container when the two members are in the second position and cannot couple to the second container when the two members are in the first position;

wherein the coupling of the second member and the coupling of the first member comprise a plurality of pawls that are adapted to engage with a neck of the second container; and wherein the pawls of the first member run in slots on the second member.

2. The connector device according to claim 1, wherein the first member comprises a guiding structure and the second member comprises a guiding structure.

3. The connector device according to claim 2, wherein the two guiding structures abut each other.

4. The connector device according to claim 2, wherein one of the guiding structures of the two members comprises a handle or grip area.

5. The connector device according to claim 2, wherein the guiding structure of one of the two members comprises one or more guiding ribs that run in guiding slots of the guiding structure of the other one of the two members.

6. The connector device according to claim 2, wherein the guiding structure of one of the two members has one or more cams that run in grooves on the guiding structure of the other one of the two members.

7. The connector device according to claim 6, wherein a stopper is provided in the one or more grooves which is able to restrict the movement of the cam in the groove in one or two directions.

8. The connector device according to claim 1, wherein a container can be coupled to the second member of the connector device when the first and second members are in the first position.

9. A septum sealed container comprising a connector device according to claim 1.

10. The septum sealed container according to claim 9, wherein the first member and the second member of the connector device are in the first position and the second member is coupled to the container.

11. A kit comprising one or more connector devices according to claim 1 and one or more septum sealed containers, wherein the couplings of the two members couple to the septum sealed containers.

12. A method for transferring liquid between two containers, the method comprising:
providing a connector device according to claim 1, the first and second members of the connector device being in the first position;
attaching the first member of the connector device to a first container, thereby penetrating a septum seal of the first container with the needle of the first member and establishing a fluid connection between first container and needle;
coupling a second container to the second member of the connector device; and
shifting the first and second members in regard to each other from the first position to the second position, thereby penetrating a septum seal of the second container with the needle of the first member and establishing a fluid connection between the second container and the needle.

13. The method according to claim 12, wherein the last two steps are reversed.

14. A connector device configured for fluidly connecting two containers, the connector device including two members that are slidably displaceable in regard to each other along an axis between a first and a second position, the connector device comprising:
a first member comprising a needle with two ends arranged parallel to the axis in such a way that a septum of a first container can be penetrated by one end of the needle when the first container is introduced into a receptacle of the first member;
a second member comprising a releasable coupling to a second container wherein the other end of the needle is configured to not come into contact with a septum of the second container coupled to the second member when the members are in the first position, and the other needle end is configured to penetrate the septum of the second container when the members are in the second position establishing a fluid connection between the two containers; and
wherein the first member comprises a releasable coupling to the second container that is coupled to the second member and wherein the coupling of the first member couples to the second container when the two members are in the second position and cannot couple of the second container when the two members are in the first position;
wherein the first member comprises a guiding structure and the second member comprises a guiding structure; and
wherein the guiding structure of at least one of the first and second members has one or more cams that run in grooves on the guiding structure of the other one of the first and second members.

15. The connector device according to claim 14, wherein at least the coupling of the second member and/or the coupling of the first member comprises a plurality of pawls that engage with a neck of the second container.

16. The connector device according to claim 14, wherein the coupling of the second member and the coupling of the first member comprise a plurality of pawls that engage with a neck of the second container.

17. The connector device according to claim 16, wherein the pawls of the first member run in slots on the second member.

18. The connector device according to claim 14, wherein the two guiding structures abut each other.

19. The connector device according to claim 14, wherein one of the guiding structures of the two members comprises a handle or a grip area.

20. The connector device according to claim 14, wherein the guiding structure of one of the two members comprises one or more guiding ribs that run in guiding slots of the guiding structure of the other one of the two members.

21. The connector device according to claim 14, wherein a stopper is provided in the one or more grooves which is able to restrict the movement of the cam in the groove in one or two directions.

22. The connector device according to claim 14, wherein a container is coupled to the second member of the connector device when the two members are in the first position.

23. A septum sealed container comprising a connector device according to claim 14.

24. The septum sealed container according to claim 23, wherein the two members of the connector device are in the first position and the second member is coupled to the container.

25. A kit comprising one or more connector devices according to claim 14 and one or more septum sealed containers, wherein the couplings of the two members couple to the septum sealed containers.

26. A method for transferring liquid between two containers, the method comprising:
providing a connector device according to claim 14, the two members of the connector device being in the first position;
attaching the first member of the connector device to a first container, thereby penetrating a septum seal of the first container with the needle of the first member and establishing a fluid connection between first container and needle;
coupling a second container to the second member of the connector device; and
shifting the two members in regard to each other from the first position to the second position, thereby penetrating a septum seal of the second container with the needle of the first member and establishing a fluid connection between the second container and the needle.

27. The method according to claim 26, wherein the last two steps are reversed.

* * * * *